US011344380B2

(12) United States Patent
Uekaji et al.

(10) Patent No.: US 11,344,380 B2
(45) Date of Patent: May 31, 2022

(54) CONTROL DEVICE FOR ROBOT SYSTEM

(71) Applicants: KAWASAKI JUKOGYO KABUSHIKI KAISHA, Kobe (JP); MEDICAROID CORPORATION, Kobe (JP)

(72) Inventors: Rikuya Uekaji, Kakogawa (JP); Tsuyoshi Tagashira, Kakogawa (JP)

(73) Assignees: KAWASAKI JUKOGYO KABUSHIKI KAISHA, Kobe (JP); MEDICAROID CORPORATION, Kobe (JP)

( * ) Notice: Subject to any disclaimer, the term of this patent is extended or adjusted under 35 U.S.C. 154(b) by 385 days.

(21) Appl. No.: 16/727,306

(22) Filed: Dec. 26, 2019

(65) Prior Publication Data
US 2020/0205918 A1 Jul. 2, 2020

(30) Foreign Application Priority Data

Dec. 26, 2018 (JP) .............................. JP2018-243454

(51) Int. Cl.
*G06F 17/00* (2019.01)
*A61B 34/37* (2016.01)
*B25J 9/00* (2006.01)
*B25J 3/04* (2006.01)
*B25J 5/00* (2006.01)
*B25J 15/04* (2006.01)
(Continued)

(52) U.S. Cl.
CPC ................. *A61B 34/37* (2016.02); *B25J 3/04* (2013.01); *B25J 5/00* (2013.01); *B25J 9/0087* (2013.01); *B25J 13/065* (2013.01); *B25J 13/081* (2013.01); *B25J 15/04* (2013.01); *A61B 2017/00973* (2013.01); *A61B 2034/305* (2016.02)

(58) Field of Classification Search
CPC ...... B25J 9/0087; B25J 13/065; B25J 13/081; B25J 15/04; B25J 9/161; A61B 2017/00973; A61B 2034/305; A61B 46/10; A61B 50/13
USPC ......................................................... 700/258
See application file for complete search history.

(56) References Cited

U.S. PATENT DOCUMENTS 5,876,325 A * 3/1999 Mizuno .................. A61B 34/37
600/117
6,208,104 B1 * 3/2001 Onoue ..................... B25J 9/161
901/6
(Continued)

FOREIGN PATENT DOCUMENTS

JP        3841762 B2    11/2006
JP     2009-278858 A    11/2009
(Continued)

*Primary Examiner* — Ronnie M Mancho
(74) *Attorney, Agent, or Firm* — Oliff PLC

(57) ABSTRACT

A control device of a robot system including a plurality of robots having servo motors of a plurality of axes. The control device includes a plurality of controllers each having a plurality of servo amplifiers that drives the servo motors of the plurality of axes of the robots, and a control unit that controls the plurality of servo amplifiers. The control unit determines a driving number of the servo motors of the plurality of axes in accordance with the robots connected to the controllers, and sets a parameter for the servo amplifiers that drive the axes of the servo motors of a number corresponding to the determined driving number.

20 Claims, 5 Drawing Sheets

(51) Int. Cl.
  *B25J 13/08*  (2006.01)
  *B25J 13/06*  (2006.01)
  *A61B 17/00*  (2006.01)
  *A61B 34/30*  (2016.01)

(56) References Cited

U.S. PATENT DOCUMENTS

| | | | | |
|---|---|---|---|---|
| 9,979,327 | B2* | 5/2018 | Tagashira | H02P 6/24 |
| 10,216,177 | B2* | 2/2019 | Gildert | G05B 19/42 |
| 10,806,534 | B2* | 10/2020 | Hashimoto | B25J 13/08 |
| 10,856,945 | B2* | 12/2020 | Hashimoto | B25J 9/0084 |
| 10,881,475 | B2* | 1/2021 | Kan | A61B 17/29 |
| 11,110,592 | B2* | 9/2021 | Shimomura | B25J 13/02 |
| 11,198,226 | B2* | 12/2021 | Kan | A61B 34/71 |
| 2004/0160206 | A1* | 8/2004 | Komaki | G05B 19/408 318/569 |
| 2011/0118874 | A1* | 5/2011 | Tanabe | B25J 9/1682 700/248 |
| 2016/0243701 | A1* | 8/2016 | Gildert | G05B 19/42 |
| 2018/0243908 | A1* | 8/2018 | Tojo | A61B 34/32 |
| 2018/0243918 | A1* | 8/2018 | Noguchi | B25J 13/084 |
| 2018/0243923 | A1* | 8/2018 | Hashimoto | B25J 13/06 |
| 2018/0257238 | A1* | 9/2018 | Hashimoto | B25J 9/1697 |
| 2018/0345492 | A1* | 12/2018 | Watanabe | B25J 9/1682 |
| 2018/0360550 | A1* | 12/2018 | Nakanishi | B25J 9/08 |
| 2019/0201021 | A1* | 7/2019 | Shelton, IV | A61B 18/12 |
| 2019/0201092 | A1* | 7/2019 | Yates | A61B 17/320068 |
| 2019/0201113 | A1* | 7/2019 | Shelton, IV | A61B 34/76 |
| 2019/0201142 | A1* | 7/2019 | Shelton, IV | A61B 18/14 |
| 2019/0358816 | A1* | 11/2019 | Saito | B25J 3/04 |
| 2020/0198125 | A1* | 6/2020 | Muneto | B25J 9/08 |
| 2020/0229882 | A1* | 7/2020 | Ito | A61B 17/3415 |
| 2020/0298408 | A1* | 9/2020 | Hashimoto | B25J 9/1664 |

FOREIGN PATENT DOCUMENTS

| | | |
|---|---|---|
| JP | 2011-108044 A | 6/2011 |
| JP | 2014-159066 A | 9/2014 |
| JP | 2016-162720 A | 9/2016 |
| JP | 2017-104452 A | 6/2017 |

* cited by examiner

CONTROL DEVICE FOR ROBOT SYSTEM

CROSS-REFERENCE TO RELATED APPLICATION

This application claims priority to and the benefit of Japanese Patent Application No. 2018-243454, filed on Dec. 26, 2018, the entire disclosure of which is incorporated herein by reference.

BACKGROUND OF THE INVENTION

(1) Field of the Invention

The present invention relates to a control device for a robot system including a plurality of robots having servo motors of a plurality of axes.

(2) Description of Related Art

Conventionally, six-axis servo control is generally used in industrial robots. For mechanical devices such as industrial robots, in a servo motor control system described in Japanese Patent No. 3841762, for example, a control device and a plurality of servo amplifiers are connected to each other with a serial bus, and a servo motor connected to the servo amplifiers is configured to be controlled. This system includes two or more types of serial bus transfer methods, and allows data transmission and reception even after the control device or one of the servo amplifiers is replaced with a new product.

SUMMARY OF THE INVENTION

In general, an articulated robot has different capacities of servo motors for each axis, and thus a pulse width modulation (PWM) carrier frequency or a parameter such as a servo parameter should be adjusted for each axis. However, the control device described in Japanese Patent No. 3841762 is not configured to set a different parameter for each axis, and therefore is not suitable for setting servo amplifiers connected to servo motors of a plurality of axes in an articulated robot. This is not a problem for only one robot but a problem common to all control devices for a robot system including a plurality of robots.

The present invention has been made to solve the above problem, and an object of the present invention is to easily set servo amplifiers connected to servo motors of a plurality of axes in a robot system including a plurality of robots.

In order to achieve the above object, a control device for a robot system according to an aspect of the present invention is a control device for a robot system including a plurality of robots having servo motors of a plurality of axes, the control device including a plurality of controllers each having a plurality of servo amplifiers that drives the servo motors of the plurality of axes of the robots, and a control unit that controls the plurality of servo amplifiers, in which the control unit determines a driving number of the servo motors of the plurality of axes in accordance with the robots connected to the plurality of controllers, and sets a parameter for the servo amplifiers that drive the axes of the servo motors of a number corresponding to the determined driving number.

In the above configuration, the control unit determines the driving number of the servo motors of the plurality of axes in accordance with the robots connected to the plurality of controllers, and sets the parameter for the servo amplifiers that drive the axes of the servo motors of the number corresponding to the determined driving number. As a result, the servo amplifiers connected to the servo motors of the plurality of axes can be easily set in the robot system including the plurality of robots.

Each of the plurality of controllers has a first connector connected to output terminals of the plurality of servo amplifiers, and the first connector may be configured to be adaptable to a connector of the servo motors included in any one of the plurality of robots.

In the above configuration, the first connector connected to the output terminals of the servo amplifiers in each controller is configured to be adaptable to the connector of the servo motors included in any one of the robots. Thus, the controller can be used as the controller for any one of the plurality of robots. Further, only one controller kept on hand as a spare facilitates a replacement of any failed controller.

The control device for the robot system further includes a coil, a connection part connected to a first end of the coil and configured to be connectable to the first connector, and a second connector connected to a second end of the coil, in which the second connector may be configured to be adaptable to the connector of the servo motors included in any one of the plurality of robots.

For example, a medical robot uses both a servo motor having a large output (for example, 400 W) and a servo motor having a small output (for example, 5 W). To perform a PWM control on a servo motor having a large output, even when the PWM carrier frequency is relatively low (for example, 8 kHz), a ripple, if any, would be so small as not to affect the control. In order to drive the servo motors having a small output in such a manner that a ripple, if any, would be so small as not to affect the control, the PWM carrier frequency should be set to 100 kHz or higher. However, the frequency cannot be increased to that extent because of restrictions such as heat generation of a motor drive element and processing speed of a calculation processing function.

In the above configuration, when the output of the servo motors is relatively small, the connection part connected to the first end of the coil is connected to the first connector connected to the output terminals of the servo amplifiers, and the second connector connected to the second end of the coil is connected to the connector of the servo motors. The coil is thus connected in series between the output terminals of the servo amplifiers and input terminals of the servo motors, and an inductance of the coil is added to an inductance of the servo motors. As a result, the servo motors can be suitably driven in such a manner that a ripple, if any, would be so small as not to affect the control.

The connection part may include the connector connected to the first end of the coil, and may be configured to be connected to the first connector via a cable connected to the connector connected to the one end of the coil.

The control device for the robot system further includes a higher-level controller that is communicably connected to the control unit in each of the plurality of controllers, and gives a command to the control unit, in which the control unit is configured to determine a driving number of the servo motors of the plurality of axes in accordance with the command from the higher-level controller, and to set the parameter for the servo amplifiers that drive the axes of the servo motors of a number corresponding to the determined driving number.

The robot system is a manipulator system for medical use, and the manipulator system includes an indication device that receives an operation input from an operator, a slave manipulator that holds a medical instrument at a distal end of the slave manipulator, and a positioner that moves an arm base holding the slave manipulator.

Further, the slave manipulator has a plurality of slave arms, and a plurality of controllers, among the plurality of controllers, corresponding to the plurality of slave arms may be configured to control an operation of the plurality of slave arms in accordance with the operation input from the operator received by the indication device.

In addition, one of the plurality of controllers corresponding to the positioner may be configured to control the operation of the positioner in accordance with the operation input received from the operator by the indication device.

Note that the manipulator system further includes a carriage that moves the positioner, in which one of the controllers corresponding to the positioner may be configured to control an operation of the carriage in accordance with the operation input from the operator received by the indication device.

Further, the indication device has a pair of master arms operated by the operator, and two controllers corresponding to the pair of master arms among the plurality of controllers may be configured to control an operation of the pair of master arms in accordance with an operation of the operator.

According to the present invention, in the robot system including the plurality of robots and having the above configuration, the servo amplifiers connected to the servo motors of the plurality of axes can be easily set.

The above object, other objects, features, and advantages of the present invention will be apparent from the following detailed description of preferred embodiments with reference to the accompanying drawings.

DETAILED DESCRIPTION OF PREFERRED EMBODIMENTS

Hereinafter, embodiments of the present invention will be described with reference to the drawings.

Embodiment

Figure 1:
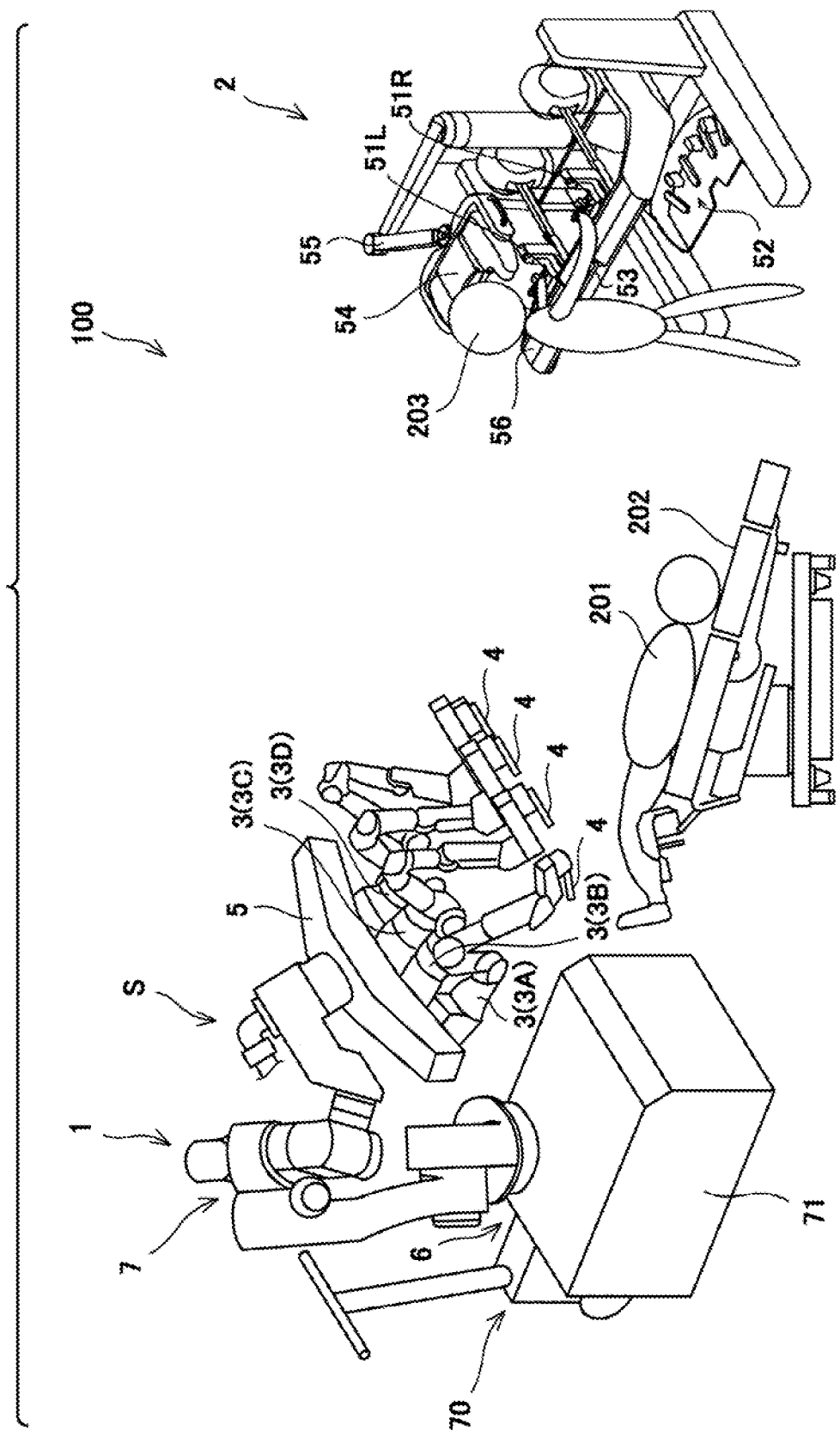
FIG. 1 shows a scene in which a robot system according to an embodiment of the present invention is used.

FIG. 1 shows a scene in which a robot system according to an embodiment of the present invention is used. As shown in FIG. 1, the robot system according to this embodiment is a manipulator system 100 for medical use used when a practitioner (operator) 203 such as a doctor performs an endoscopic surgery on a patient 201 on an operating table 202 during a surgery such as a robot-assisted surgery or a remote robot surgery.

The manipulator system 100 includes a slave manipulator 1 as a patient-side system, and an indication device 2 that operates the slave manipulator 1. The indication device 2 is disposed apart from the slave manipulator 1, and the slave manipulator 1 is remotely operated by the indication device 2. The practitioner 203 inputs an operation to be performed by the slave manipulator 1 to the indication device 2, and the indication device 2 transmits this operation command to the slave manipulator 1. The slave manipulator 1 receives the operation command transmitted from the indication device 2, and on the basis of this operation command, operates a long shaft-shaped medical instrument 4 such as an endoscope assembly or an instrument included in the slave manipulator 1.

The indication device 2 configures an interface between the manipulator system 100 and the practitioner 203, and is a device that operates the slave manipulator 1. The indication device 2 is disposed inside or outside the operating room. The indication device 2 includes a pair of master arms 51R and 51L that the practitioner 203 operates to input an operation command, an operation pedal 52, a touch panel 53, a monitor 54 that displays an image captured by the endoscope assembly, a support arm 55 that supports the monitor 54 at a height position of the face of the operator such as a doctor, and a bar 56 on which the touch panel 53 is disposed. Each of the pair of master arms 51R and 51L is configured as a seven-axis articulated arm in this embodiment. The pair of master arms 51R and 51L is configured to be operated by the practitioner 203 and to operate in accordance with the operation. The practitioner 203 operates the left and right master arms 51L and 51R and the operation pedal 52 to input the operation command to the indication device 2 while visually recognizing an affected part with the monitor 54. The operation command input to the indication device 2 is transmitted to a control device 6 of the manipulator system 100 by wire or wirelessly. The operation of the slave manipulator 1 is controlled by the control device 6. The control device 6 is configured by a computer such as a microcontroller. The control device 6 is installed, for example, inside a base body 71 of a carriage 70. A servo motor for driving is attached to wheels of the carriage 70, and the carriage 70 may be configured to operate in accordance with an operation input received by the indication device 2 from the operator.

The slave manipulator 1 configures an interface between the manipulator system 100 and the patient 201. The slave manipulator 1 is disposed in the sterilized operating room that is a sterile field. In FIG. 1, the slave manipulator 1 includes a positioner 7, an elongated arm base 5 attached to a distal end of the positioner 7, and a plurality of slave arms (in this embodiment, four slave arms) 3 of which base end is detachably attached to the arm base 5, with multiple degrees of freedom. The slave manipulator 1 is configured such that the plurality of slave arms 3 is in a folded storage posture.

The positioner 7 is configured as a seven-axis vertical articulated robot in this embodiment. The positioner 7 is provided on the base body 71 of the carriage 70 disposed at a predetermined position in the operating room, and can move a position of the arm base 5 three-dimensionally. The slave arms 3 and the arm base 5 are covered with a sterile drape (not shown), and the slave arms 3 and the arm base 5 are shielded from the sterile field in the operating room.

In this embodiment, each of the slave arms 3 is configured as an eight-axis articulated arm. At a distal end of a slave arm 3A among the plurality of slave arms 3, for example, a replacement instrument (for example, forceps) is held as the medical instrument 4. At a distal end of a slave arm 3B, an instrument such as forceps is held as the medical instrument 4. Further, at a distal end of a slave arm 3C, an endoscope assembly, for example, is held as the medical instrument 4.

At a distal end of a slave arm 3D, a replacement endoscope assembly, for example, is held as the medical instrument 4. Each slave arm 3 has a drive unit that drives the medical instrument 4 in this embodiment.

In the slave manipulator 1, the arm base 5 has a function as a hub serving as a base for the plurality of slave arms 3. In this embodiment, the positioner 7 and the arm base 5 configure a manipulator arm support S that movably supports the plurality of slave arms 3.

As described above, the manipulator system 100 includes the pair of master arms 51R and 51L, the four slave arms 3A to 3D, and the positioner 7 that moves the arm base 5 holding the four slave arms 3A to 3D as a plurality of robots. In preparation for a surgery using the manipulator system 100, first, an assistant operates an operation device (not shown) provided in the patient-side system such that the arm base 5 and the operating table 202 or the patient 201 have a predetermined positional relationship. Then, the positioner 7 is operated to position the arm base 5. Next, the assistant operates an arm operating device (not shown) provided on each slave arm 3 such that the medical instrument 4 and a sleeve (cannula sleeve) placed on the body surface of the patient 201 have a predetermined initial positional relationship. Then, each slave arm 3 is operated to position the medical instrument 4. Then, the control device 6 operates the medical instrument 4 by each slave arm 3 in accordance with the operation command from the indication device 2 to change a displacement and a posture of the medical instrument 4 as appropriate for performance of an operation, while the positioner 7 is kept stationary in principle.

Figure 2:
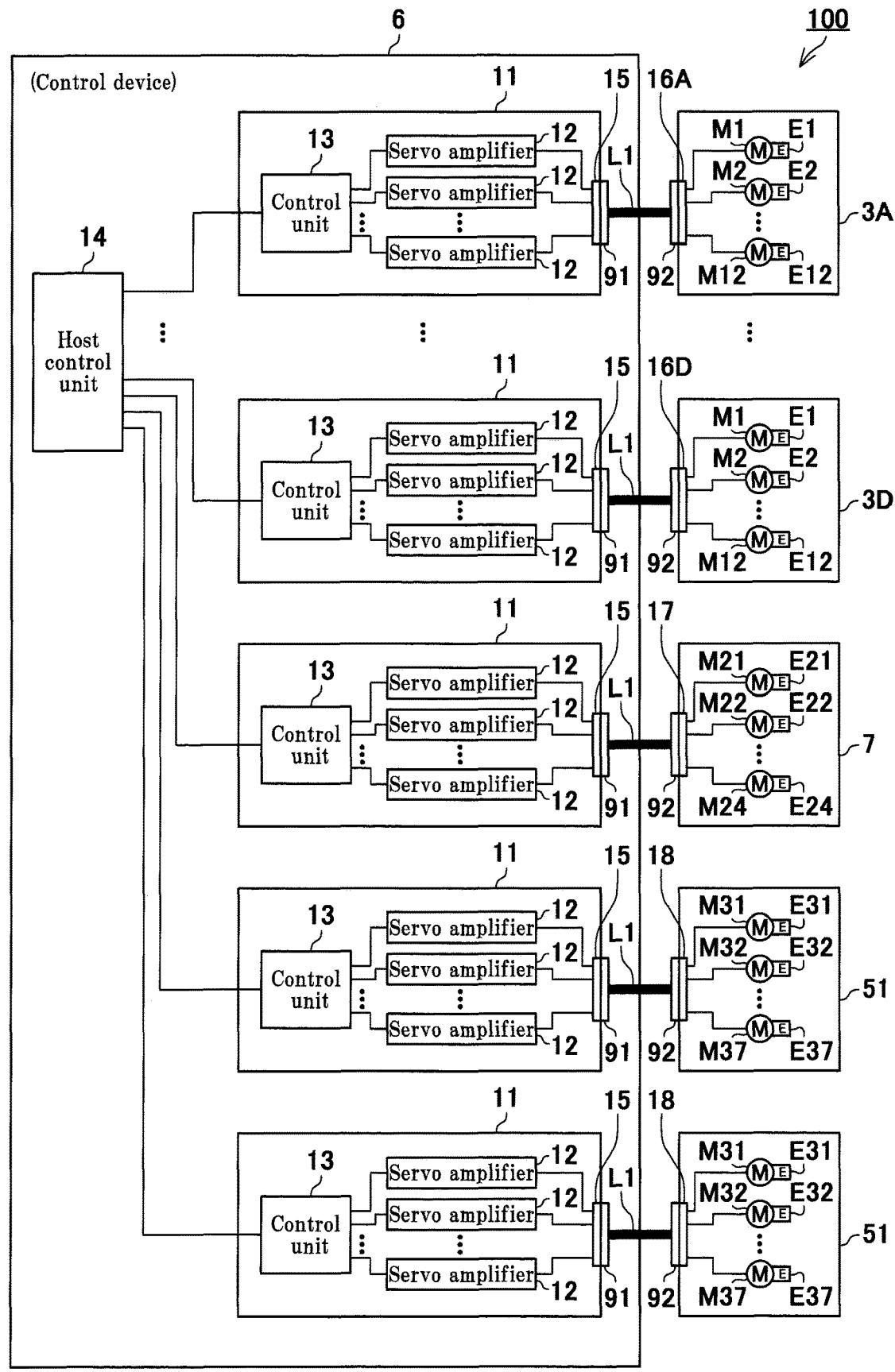
FIG. 2 is a block diagram showing a configuration of a control device for the robot system in FIG. 1.

Next, a configuration of the control device 6 will be described with reference to the block diagram of FIG. 2. As shown in FIG. 2, the control device 6, the four slave arms 3A to 3D, the pair of master arms 51R and 51L, and the positioner 7 as the robots are connected via a cable L1 configured by including a motor power line that supplies power to servo motors M of each robot, and a signal line that transmits a detection signal from encoders E and other sensors. A connector 91 and a connector 92 are provided at both ends of the cable L1. The connector 91 is a controller-side connector, and the connector 92 is a motor-side connector. The control device 6 is configured to drive a plurality of servo motors M included in each robot. Further, although the servo motors M have three phases, the number of phases does not particularly limit the present invention, and the phase may be, for example, single, and the power line and the signal line may be different cables.

The slave arm 3A is provided with, corresponding to the eight joints and the drive unit (medical instrument 4), 12 servo motors M1 to M12 for driving, encoders E1 to E12 that detect rotation angles of the servo motors M1 to M12, and a speed reducer (not shown) that reduces an output of the servo motors M1 to M12 to increase torque. An operation with the medical instrument 4 (for example, forceps) at each distal end of the slave arms 3A to 3D requires a delicate movement (see FIG. 1). Thus, servo motors having a relatively small output (for example, 5 W) are used as the 12-axis servo motors M1 to M12 of the slave arms 3A to 3D. Similarly, the other slave arms 3B to 3D are provided with, corresponding to the eight joints and the drive unit (medical instrument 4), the 12 servo motors M1 to M12 for driving, the encoders E1 to E12 that detect the rotation angles of the servo motors M1 to M12, and the speed reducer (not shown) that reduces the output of the servo motors M1 to M12 to increase torque. In the following, the plurality of servo motors may be collectively referred to as the servo motors M. A plurality of encoders may be collectively referred to as the encoders E.

The positioner 7 is provided with, corresponding to the seven joints, seven servo motors M21 to M27 for driving, encoders E21 to E27 that detect rotation angles of the servo motors M21 to M27, and a speed reducer (not shown) that reduces an output of the servo motors M21 to M27 to increase torque. The positioner 7 is configured to move the arm base 5 holding the four slave arms 3A to 3D (see FIG. 1). Thus, servo motors having a relatively large output (for example, 400 W) are used as the seven-axis servo motors M21 to M27 of the positioner 7.

One master arm 51R is provided with, corresponding to seven joints, seven servo motors M31 to M37 for driving, encoders E31 to E37 that detect rotation angles of the servo motors M31 to M37, and a speed reducer (not shown) that reduces an output of the servo motors M31 to M37 to increase torque. Similarly, the other master arm 51L is provided with, corresponding to the seven joints, the seven servo motors M31 to M37 for driving, the encoders E31 to E37 that detect the rotation angles of the servo motors M31 to M37, and the speed reducer (not shown) that reduces the output of the servo motors M31 to M37 to increase torque. The pair of master arms 51R and 51L are operated with both hands of the practitioner (operator) 203 (see FIG. 1). Thus, servo motors having a relatively small output (for example, 5 W) are used as the servo motors M on a distal end side (operator side) of the master arms 51R and 51L. On the other hand, servo motors having a relatively large output (for example, 400 W) are used as the servo motors M on a base end side of the master arms 51R and 51L.

The control device 6 includes seven controllers 11 and a higher-level controller 14 communicably connected to each of the controllers 11. Each controller 11 has 12 servo amplifiers 12 capable of driving the servo motors M of a maximum of 12 axes, and a control unit 13 capable of controlling the servo amplifiers 12. Each controller 11 is configured to be capable of performing a pulse width modulation (PWM) control on the servo motors M of a maximum of 12 axes. The control unit 13 of each controller 11 and the higher-level controller 14 are configured by a device having a calculation processing function and a memory, such as a computer, a microcontroller, and a microprocessor. The control unit 13 as a calculation processing unit executes a predetermined program stored in the memory of the device, and thereby each function is achieved. In this embodiment, the control unit 13 is configured to execute, for example, a program for a setting operation or a program for a normal operation to perform the operation.

Each of the seven controllers 11 has a connector 15 connected to output terminals of the 12 servo amplifiers 12. The connector 15 is configured to be adaptable to a connector of the servo motors included in any one of the plurality of robots.

The connector 15 of a first controller 11 is connected via the cable L1 to a connector 16A of the 12-axis servo motors M1 to M12 included in the slave arm 3A. In the first controller 11, the 12 servo amplifiers 12 are configured to drive the 12-axis servo motors M1 to M12 of the slave arm 3A in accordance with a control command generated by the control unit 13.

The connectors 15 of second to fourth controllers 11 are respectively connected via cables L1 to connectors 16B to 16D of the 12-axis servo motors M1 to M12 included in the slave arms 3B to 3D. In each of the second to fourth controllers 11, similarly to the first controller 11, the 12 servo amplifiers 12 are configured to control the 12-axis servo motors M1 to M12 of the slave arms 3B to 3D in accordance with the control command generated by the control unit 13. In the normal operation, the first to fourth controllers 11 corresponding to the slave arms 3A to 3D are configured to control the operations of the slave arms 3A to 3D in accordance with the operation input from the practitioner 203 received by the indication device 2.

The connector 15 of a fifth controller 11 is connected via the cable L1 to a connector 17 of the seven-axis servo motors M21 to M27 included in the positioner 7. In the fifth controller 11, the seven servo amplifiers 12 are configured to drive the seven-axis servo motors M21 to M27 of the positioner 7 in accordance with the control command generated by the control unit 13. In the normal operation, the fifth controller 11 corresponding to the positioner 7 is configured to control the operation of the positioner 7 in accordance with the operation input from the practitioner 203 received by the indication device 2. In the normal operation, the fifth controller 11 may be configured to control the operation of the carriage 70 (servo motor attached to the wheels) by the rest of the servo amplifiers 12 in accordance with the operation input from the practitioner 203 received by the indication device 2.

The connector 15 of a sixth controller 11 is connected via the cable L1 to a connector 18 of the seven-axis servo motors M31 to M37 included in the one master arm 51R. In the sixth controller 11, the seven servo amplifiers 12 are configured to drive the seven-axis servo motors M31 to M37 of the one master arm 51R in accordance with the control command generated by the control unit 13. The connector 15 of a seventh controller 11 is connected via the cable L1 to the connector 18 of the seven-axis servo motors M31 to M37 included in the other master arm 51L. Also, in the seventh controller 11, the seven servo amplifiers 12 are configured to drive the seven-axis servo motors M31 to M37 of the other master arm 51L in accordance with the control command generated by the control unit 13. In the normal operation, the sixth controller 11 and the seventh controller 11 corresponding to the pair of master arms 51R and 51L are configured to control the operation of the pair of master arms 51R and 51L in accordance with the operation from the practitioner 203.

The higher-level controller 14 is configured to transmit and receive data to and from each controller 11 and to control the entire manipulator system 100. In this embodiment, the manipulator system 100 is controlled by a known parallel bilateral control method. Here, the manipulator system 100 includes, for example, a force sensor (not shown) capable of detecting an operating force applied to the master arms 51R and 51L by the practitioner 203, and a force sensor (not shown) capable of detecting a reaction force applied to the medical instrument 4. The higher-level controller 14 generates an operation command for the master arms 51R and 51L on the basis of the operating force applied to the master arms 51R and 51L and the reaction force applied to the medical instrument 4, and generates an operation command for the slave arms 3A to 3D. The sixth controller 11 and the seventh controller 11 are configured to control the master arms 51R and 51L on the basis of the operation command for the master arms 51R and 51L generated by the higher-level controller 14. The first to fourth controllers 11 are configured to control the slave arms 3A to 3D on the basis of the operation command for the slave arms 3A to 3D generated by the higher-level controller 14. Thus, in the normal operation, the control device 6 operates the medical instrument 4 by each of the slave arms 3A to 3D in accordance with the operation command from the master arms 51R and 51L (indication device 2) to appropriately change the displacement and posture of the medical instrument 4.

Next, an example of a setting operation of each controller 11 at a time of initial setting of the control device 6 will be described with reference to a flowchart of FIG. 3. The program for the setting operation is stored in advance in each controller 11 (memory). In this embodiment, each controller 11 is configured to perform the setting operation by executing the program for the setting operation. Thus, the setting operation is common to all the controllers 11. Here, for convenience, only the setting operation of the fifth controller 11 connected to the positioner 7 (see FIG. 2), for example, will be described. FIG. 4 is a diagram showing a configuration of the output side of the fifth controller 11.

Figure 3:
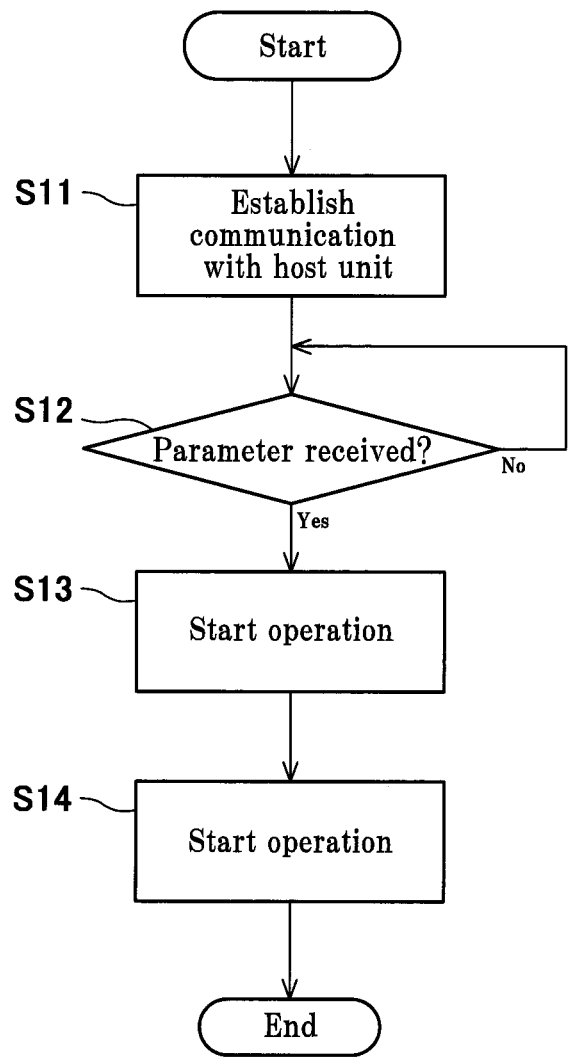
FIG. 3 is a flowchart showing an example of a setting operation of a controller at a time of initial setting of the control device in FIG. 2.
Figure 4:
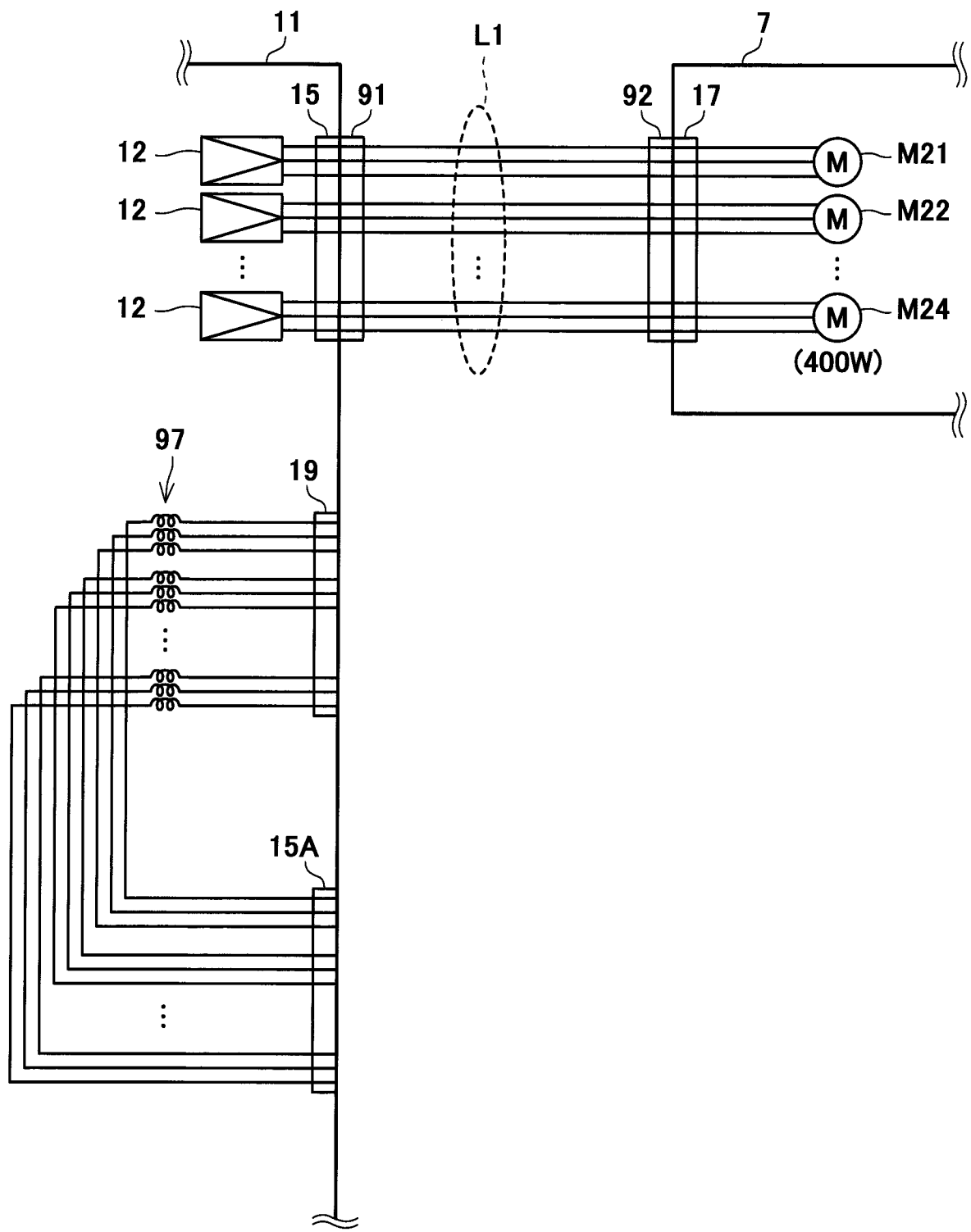
FIG. 4 shows a configuration of an output side of a controller connected to a positioner.

First, a communication path is established between the control unit 13 and the higher-level controller 14 (step S11 in FIG. 3). At this time, the higher-level controller 14 reads out, from the memory, a parameter for setting the seven servo amplifiers 12 that drive the seven-axis servo motors M21 to M27 of the positioner 7, and transmits the parameter to the fifth controller 11. In this embodiment, the program for the normal operation of each robot connected to each controller 11 is stored in advance in the memory (not shown) of the higher-level controller 14. Here, the higher-level controller 14 reads out the program for the normal operation of the positioner 7 from the memory and transmits the program to the fifth controller 11 together with the parameter.

Next, the control unit 13 receives the parameter for setting the servo amplifiers 12 from the higher-level controller 14 (step S12 in FIG. 3). The parameter for setting the servo amplifiers 12 includes the number of servo motors, the output (capacity) of the servo motors, the PWM carrier frequency for each axis, a servo parameter for each axis, and other parameters. The servo amplifiers 12 are configured to perform auto-tuning to facilitate servo adjustment, and the parameter for the servo amplifiers 12 may include information necessary for auto-tuning performed for each axis. In the auto-tuning, first, inertia, which is a weight of a workpiece to be moved, is automatically estimated from a load status of each axis, and a value of a responsiveness setting is increased or decreased, whereby the related servo parameter is automatically adjusted collectively.

The control unit 13 determines a driving number of the servo motors on the basis of the command received from the higher-level controller 14, and sets the parameter for the servo amplifiers 12 that drive the axes of the servo motors of the number corresponding to the determined driving number (step S13 in FIG. 3). Here, the control unit 13 sets the parameter for the servo amplifiers 12 that drive the four-axis servo motors M21 to M24 of the positioner 7. The positioner 7 is configured to move the arm base 5 holding the four slave arms 3A to 3D (see FIG. 1). Thus, servo motors having a relatively large output (for example, 400 W) are used as the four-axis servo motors M21 to M24 of the positioner 7. The PWM carrier frequency is set to, for example, 20 kHz.

In the other controllers 11, similarly, the control unit 13 determines the driving number of the servo motors of a plurality of axes in accordance with the robots connected to the controller, and sets the parameter for the servo amplifiers 12 that drive the axes of the servo motors of a number corresponding to the determined driving number. Subsequently, the normal operation program is executed in each controller 11, and the normal operation of the manipulator system 100 is started (step S14 in FIG. 3).

In this embodiment, in the manipulator system 100, the control unit 13 determines the driving number of the servo motors on the basis of the command from the higher-level controller 14 during the setting operation (when the setting operation program is executed). Then, the control unit 13 sets the parameter for the servo amplifiers 12 that drive the axes of the servo motors of a number corresponding to the determined driving number. Thus, the servo amplifiers 12 can be easily set.

Further, in this embodiment, the connector 15 connected to the output terminals of the 12 servo amplifiers 12 in each controller 11 is configured to be adaptable to the connectors 16A to 16D, 17, 18, and 18 of the servo motors included in any of the robots (see FIG. 2) among the plurality of the robots (3A to 3D, 7, 51R, 51L in FIG. 2). Thus, each controller 11 can be used as the controller 11 for any one of the robots. Further, only one controller kept on hand as a spare facilitates a replacement of any failed controller. Note that the setting operation of each controller 11 is not limited to the initial setting of the control device 6, but is similar when only one controller 11 is replaced.

FIG. 4 shows a configuration of the output side of the fifth controller 11 connected to the seven-axis servo motors M21 to M27 of the positioner 7. As shown in FIG. 4, each controller 11 includes a connector 15 connected to the output terminals of the 12 servo amplifiers 12, a coil 97, a connector 19 connected to a first end of the coil 97, and a connector 15A connected to a second end of the coil 97. The connector 15 of each controller 11 is connected via the cable L1 to the connector 17 of the seven-axis servo motors M21 to M27 included in the positioner 7. As the seven-axis servo motors M21 to M27 of the positioner 7, servo motors having a relatively large output (for example, 400 W) are used. Here, when the PWM carrier frequency is set relatively low (for example, 8 kHz), a ripple, if any, would be so small as not to affect the control. However, the frequency is set to an extent to exceed an audible frequency (for example, 20 kHz) in order to avoid making a noise. The coil 97 is provided inside each controller 11. The connector 15A is configured to be adaptable to the connector of the servo motors included in any one of the plurality of robots.

Figure 5:
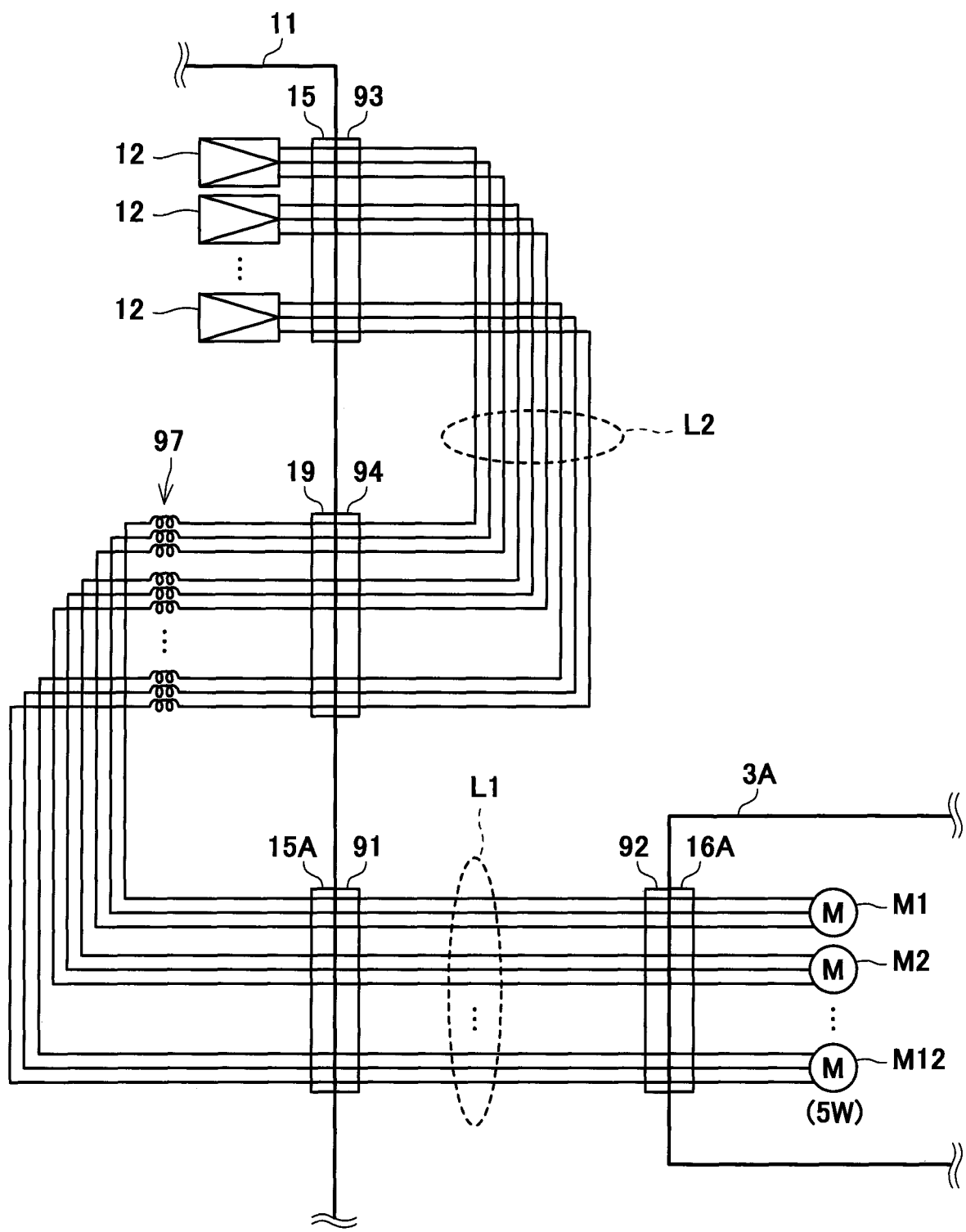
FIG. 5 shows a configuration of the output side of a controller connected to a slave arm.

FIG. 5 shows a configuration of the output side of the first controller 11 connected to the 12-axis servo motors M1 to M12 of the slave arm 3A. As the 12-axis servo motors M1 to M12 of the slave arm 3A, servo motors having a relatively small output (for example, 5 W) are used. In order to drive the servo motors M1 to M12 having a small output in such a manner that a ripple, if any, would be so small as not to affect the control, the PWM carrier frequency should be set to 100 kHz or higher. However, the frequency cannot be increased to that extent because of restrictions such as heat generation of a motor drive element and processing speed of the calculation processing function.

Therefore, in FIG. 5, the connector 19 connected to the first end of the coil 97 is connected to the connector 15 via a cable L2. A connector 93 and a connector 94 are provided at both ends of the cable L2. The connector 93 is a controller-side connector, and the connector 94 is a coil-side connector. On the other hand, the connector 15A connected to the second end of the coil 97 is connected to the connector 16A of the servo motors M1 to M12 via the cable L1. The coil 97 is thus connected in series between the output terminals of the 12 servo amplifiers 12 and the input terminals of the servo motors M1 to M12, and an inductance of the coil 97 is added to an inductance of the servo motors M1 to M12. As a result, the servo motors can be suitably driven in such a manner that a ripple, if any, would be so small as not to affect the control.

Servo motors having a relatively small output (for example, 5 W) are used as the servo motors M on the distal end side (operator side) of the master arms 51R and 51L, and servo motors having a relatively large output (for example, 400 W) are used as the servo motors M on the base end side of the master arms 51R and 51L. That is, a difference in the capacity of the servo motors in the master arms 51R and 51L is remarkable for each axis. In this case, only the servo motors having a relatively small output located at the distal end side of the master arms 51R and 51L may be configured to be connected to the coil 97 in the sixth controller 11 and the seventh controller 11.

In this embodiment, the coil 97 is provided inside each controller 11, but may be provided outside each controller 11 as long as the control device 6 includes the coil 97. Further, the coil 97 is configured to be connected to the connector 15 via the connector 19 connected to the first end of the coil 97 and the cable L2, but may be connected to the connector 15 via a jumper wire, for example.

The manipulator system 100 according to this embodiment is controlled by the parallel bilateral control method, but is not limited thereto.

Other Embodiments

In this embodiment, the control unit 13 in each of the plurality of controllers 11 is configured to determine the driving number of the servo motors M of the plurality of axes on the basis of the command from the higher-level controller 14, and to set the parameter for the servo amplifiers 12 that drive the axes of the servo motors of a number corresponding to the determined driving number (see FIG. 3). However, the configuration is not limited thereto as long as the control unit 13 is configured to set the parameter in accordance with the robots connected to the plurality of controllers 11. For example, a configuration may be provided in which information for setting a parameter for the servo amplifiers 12 can be directly input to each controller 11, or a configuration may be provided in which information can be read from outside (for example, from the robot side).

Note that the robot system according to this embodiment includes the seven robots (controllers). However, the configuration is not limited to this as long as the configuration includes a plurality of robots. Further, in this embodiment, each slave arm 3 is configured as the eight-axis articulated arm, but may be configured as an articulated arm having joints of seven or more axes. In this embodiment, each of the pair of master arms 51R and 51L is configured as the seven-axis articulated arm, but may be configured as an articulated arm having joints of a plurality of axes. In this embodiment, the positioner 7 is configured as the seven-axis vertical articulated robot, but may be configured as an articulated robot having joints of a plurality of axes.

The robot system according to this embodiment is configured by a master-slave type manipulator system 100 in which the plurality of slave arms 3 is remotely operated by the pair of master arms 51R and 51L, but may be a robot system including a plurality of robots having servo motors of a plurality of axes. For example, in a semiconductor processing facility, the robot system according to this embodiment may be a robot system including a plurality of horizontal articulated robots for transporting substrates.

The present invention is useful in a robot system including a plurality of robots having servo motors of a plurality of axes.

From the above description, many modifications and other embodiments of the present invention are apparent to a person skilled in the art. Therefore, the above description should be construed as illustrative only and is provided for the purpose of teaching a person skilled in the art the best mode of carrying out the present invention. The details of the structure and/or function can be substantially changed without departing from the spirit of the present invention.

What is claimed is:

1. A control device for a robot system including a plurality of robots having servo motors of a plurality of axes,
the control device comprising a plurality of controllers each having a plurality of servo amplifiers that drives the servo motors of the plurality of axes of the robots, and a control unit that controls the plurality of servo amplifiers,
wherein the control unit is configured to determine a driving number of the servo motors of the plurality of axes in accordance with the robots connected to the plurality of controllers, and to set a parameter for the servo amplifiers that drive the axes of the servo motors of a number corresponding to the determined driving number.

2. The control device for the robot system according to claim 1,
wherein each of the plurality of controllers has a first connector connected to output terminals of the plurality of servo amplifiers, and
the first connector is configured to be adaptable to a connector of the servo motors included in any one of the plurality of robots.

3. The control device for the robot system according to claim 2, further comprising:
a coil;
a connection part connected to a first end of the coil and configured to be connectable to the first connector; and
a second connector connected to a second end of the coil,
wherein the second connector is configured to be adaptable to the connector of the servo motors included in any one of the plurality of robots.

4. The control device for the robot system according to claim 1, further comprising:
a higher-level controller that is communicably connected to the control unit in each of the plurality of controllers, and gives a command to the control unit,
wherein the control unit is configured to determine a driving number of the servo motors of the plurality of axes in accordance with the command from the higher-level controller, and to set the parameter for the servo amplifiers that drive the axes of the servo motors of a number corresponding to the determined driving number.

5. The control device for the robot system according to claim 1,
wherein the robot system is a manipulator system for medical use, and
the manipulator system includes
an indication device that receives an operation input from an operator,
a slave manipulator that holds a medical instrument at a distal end of the slave manipulator, and
a positioner that moves an arm base holding the slave manipulator.

6. The control device for the robot system according to claim 5,
wherein the slave manipulator has a plurality of slave arms, and
a plurality of controllers, among a plurality of controllers, corresponding to the plurality of slave arms is configured to control an operation of the plurality of slave arms in accordance with the operation input from the operator received by the indication device.

7. The control device for the robot system according to claim 5,
wherein the manipulator system includes an operation device with which the operator operates the positioner, and
one controller, among the plurality of controllers, corresponding to the positioner is configured to control an operation of the positioner in accordance with the operation input from the operator received by the operation device.

8. The control device for the robot system according to claim 7,
wherein the manipulator system further includes a carriage that moves the positioner, and
the one controller corresponding to the positioner is configured to control an operation of the carriage in accordance with the operation input from the operator received by the operation device.

9. The control device for the robot system according to claim 5,
wherein the indication device has a master arm operated by the operator, and
a controller corresponding to the master arm among the plurality of controllers is configured to control an operation of the master arm in accordance with the operation of the operator.

10. A medical manipulator system comprising:
a first slave arm that is configured to hold a first medical instrument at a distal end of the first slave arm, and has joints of a plurality of axes and a plurality of servo motors provided for each of the joints of the plurality of axes;
a second slave arm that is configured to hold a second medical instrument at a distal end of the second slave arm, and has joints of a plurality of axes and a plurality of servo motors provided for each of the joints of the plurality of axes;
a first controller having a plurality of servo amplifiers that drives the plurality of servo motors of the first slave arm, and a first control unit that controls the plurality of servo amplifiers; and
a second controller having a plurality of servo amplifiers that drives the plurality of servo motors of the second slave arm, and a second control unit that controls the plurality of servo amplifiers,
wherein the first control unit is configured to determine a driving number of the plurality of servo motors in accordance with the first slave arm connected to the first controller, and to set a parameter for the servo amplifiers that drive the servo motors of a number corresponding to the determined driving number, and
the second control unit is configured to determine a driving number of the plurality of servo motors in accordance with the second slave arm connected to the second controller, and to set a parameter for the servo amplifiers that drive the servo motors of a number corresponding to the determined driving number.

11. The medical manipulator system according to claim 10, further comprising an indication device that receives an operation input from an operator,
wherein the first controller is configured to control an operation of the first slave arm in accordance with the operation input from the operator received by the indication device, and
the second controller is configured to control an operation of the second slave arm in accordance with the operation input from the operator received by the indication device.

12. The medical manipulator system according to claim 10, wherein each of the first and second slave arms includes a medical instrument that is replaceable and a drive unit that drives the medical instrument at each distal end of the first and second slave arms.

13. The medical manipulator system according to claim 10, wherein each of the first and second slave arms is an articulated arm having joints of seven or more axes.

14. The medical manipulator system according to claim 10, further comprising:
a positioner having joints of a plurality of axes and a plurality of servo motors provided for each of the joints of the plurality of axes, the joints moving an arm base holding the first and second slave arms; and
a third controller having a plurality of servo amplifiers that drives the plurality of servo motors of the positioner, and a third control unit that controls the plurality of servo amplifiers,
wherein the third control unit is configured to determine a driving number of the plurality of servo motors in accordance with the positioner connected to the third controller, and to set a parameter for the servo amplifiers that drive the servo motors of a number corresponding to the determined driving number.

15. The medical manipulator system according to claim 11,
wherein the indication device has a first master arm and a second master arm operated by the operator, and
each of the first master arm and the second master arm has joints of a plurality of axes and a plurality of servo motors provided for each of the joints of the plurality of axes.

16. The medical manipulator system according to claim 11, wherein the indication device further includes an operation pedal and a touch panel that are operated by the operator.

17. The medical manipulator system according to claim 15, further comprising:
a third controller having a plurality of servo amplifiers that drives the plurality of servo motors of the first master arm, and a third control unit that controls the plurality of servo amplifiers; and
a fourth controller having a plurality of servo amplifiers that drives the plurality of servo motors of the second master arm, and a fourth control unit that controls the plurality of servo amplifiers,
wherein the third control unit is configured to determine a driving number of the plurality of servo motors in accordance with the first master arm connected to the third controller, and to set a parameter for the servo amplifiers that drive the servo motors of a number corresponding to the determined driving number, and
the fourth control unit is configured to determine a driving number of the plurality of servo motors in accordance with the second master arm connected to the fourth controller, and to set a parameter for the servo amplifiers that drive the servo motors of a number corresponding to the determined driving number.

18. The medical manipulator system according to claim 14, further comprising an operation device with which an operator operates the positioner,
wherein the third controller corresponding to the positioner is configured to control an operation of the positioner in accordance with an operation input from the operator received by the operation device.

19. The medical manipulator system according to claim 18, further comprising a carriage that moves the positioner,
wherein the third controller corresponding to the positioner is configured to control an operation of the carriage in accordance with the operation input from the operator received by the operation device.

20. A method of controlling a robot system by a control device,
the robot system including a plurality of robots having servo motors of a plurality of axes,
the control device including a plurality of controllers each having a plurality of servo amplifiers that drives the servo motors of the plurality of axes of the robots, and a control unit that controls the plurality of servo amplifiers,
the method comprising the steps of:
determining a driving number of the servo motors of the plurality of axes by the control unit in accordance with the robots connected to the plurality of controllers; and
setting a parameter for the servo amplifiers that drive the axes of the servo motors of a number corresponding to the determined driving number.

* * * * *